(12) United States Patent
Carl et al.

(10) Patent No.: US 8,391,570 B2
(45) Date of Patent: Mar. 5, 2013

(54) METHOD OF GUIDING AN IRRADIATION EQUIPMENT

(75) Inventors: Jesper Carl, Nibe (DK); Henrik Harboe, Holte (DE); Erik Othel-Jacobsen, Hellebæk (DK)

(73) Assignee: PNN Medical A/S, Kvistgard (DK)

( * ) Notice: Subject to any disclaimer, the term of this patent is extended or adjusted under 35 U.S.C. 154(b) by 1199 days.

(21) Appl. No.: 11/988,416

(22) PCT Filed: Jun. 30, 2006

(86) PCT No.: PCT/DK2006/000387
§ 371 (c)(1),
(2), (4) Date: Apr. 4, 2008

(87) PCT Pub. No.: WO2007/006303
PCT Pub. Date: Jan. 18, 2007

(65) Prior Publication Data
US 2008/0317312 A1     Dec. 25, 2008

Related U.S. Application Data

(60) Provisional application No. 60/697,534, filed on Jul. 11, 2005.

(30) Foreign Application Priority Data

Jul. 8, 2005   (EP) .................................. 05014893

(51) Int. Cl.
*G01K 9/20*     (2006.01)
*A61B 5/05*     (2006.01)
(52) U.S. Cl. ........... 382/128; 382/154; 600/424; 378/64
(58) Field of Classification Search .......... 382/128–133; 600/407–464; 250/422.11
See application file for complete search history.

(56) References Cited

U.S. PATENT DOCUMENTS

| 5,853,366 A | 12/1998 | Dowlatshahi |
| 6,230,038 B1 | 5/2001 | von Gutfeld et al. |

(Continued)

FOREIGN PATENT DOCUMENTS

| JP | 2000-167072 A | 6/2000 |
| JP | 2005-125080 A | 5/2005 |

(Continued)

OTHER PUBLICATIONS

Kompatsiaris et al., "Deformable Boundary Detection of Stents in Angiographic Images," IEEE Transactions on Medical Imaging, vol. 19, No. 6, Jun. 2000, pp. 652-662.

(Continued)

*Primary Examiner* — Melissa Koval
*Assistant Examiner* — Emily Chan
(74) *Attorney, Agent, or Firm* — Birch, Stewart, Kolasch & Birch, LLP

(57) ABSTRACT

The present invention relates to a method and an apparatus for guiding an irradiation equipment (2) located outside a human body (1) or an animal body. The method comprises the steps of identifying, in an image (4), a three-dimensional element (7) visible in the image (4), said three-dimensional element (7) has been in position in, or being inserted into, a cavity of the human body (1) or the animal body, establishing, in the image (4), a preliminary position of the three-dimensional element (7) visible in the image (4) in relation to a reference, establishing a preliminary position of the irradiation equipment (2) in relation to the reference, and adjusting the irradiation equipment (2) in response to the position the three-dimensional element (7).

33 Claims, 11 Drawing Sheets

U.S. PATENT DOCUMENTS

| | | |
|---|---|---|
| 6,251,135 B1 | 6/2001 | Stinson et al. |
| 6,307,914 B1 | 10/2001 | Kunieda et al. |
| 6,405,072 B1 * | 6/2002 | Cosman .................. 600/426 |
| 6,537,195 B2 | 3/2003 | Forman |
| 6,628,982 B1 | 9/2003 | Thomas et al. |
| 7,657,303 B2 * | 2/2010 | Mate et al. ................ 600/424 |
| 2001/0004395 A1 | 6/2001 | McCrory et al. |
| 2004/0138555 A1 * | 7/2004 | Krag et al. ................ 600/424 |
| 2005/0033149 A1 * | 2/2005 | Strommer et al. .......... 600/407 |
| 2005/0063908 A1 | 3/2005 | Burbank et al. |

FOREIGN PATENT DOCUMENTS

| | | |
|---|---|---|
| RU | 2171630 C2 | 8/2001 |
| WO | WO-93/13824 A1 | 7/1993 |
| WO | WO-99/27839 A2 | 6/1999 |
| WO | WO-02/19908 A1 | 3/2002 |
| WO | WO-02/089915 A1 | 11/2002 |
| WO | WO-02/100485 A1 | 12/2002 |
| WO | WO 2004/032779 A1 | 4/2004 |

OTHER PUBLICATIONS

Berbeco et al., "Towards tumor tracking in the absence of radiopaque markers," Massachusetts General Hospital and Harvard Medical School, Boston, MA.

"UMC Utrecht demonstrates automatic marker detection with amorphous-silicon imager," Wavelength, vol. 5., No. 2, Jul. 2001.

Carl et al., "Feasibility study using a Ni-Ti stent and electronic portal imaging to localize the prostate during radiotherapy", Radiotherapy and Oncology, vol. 78, 2006, pp. 199-206.

Hawkes, "Registration Methodology", Section 1, Medical Image Registration, Chapter 2, 2001, pp. 11-38.

Hill et al., "Registration of MR and CT Images for Clinical Applications", Medical Image Registration, Chapter 10, 2001, pp. 217-232.

* cited by examiner

7

7

7

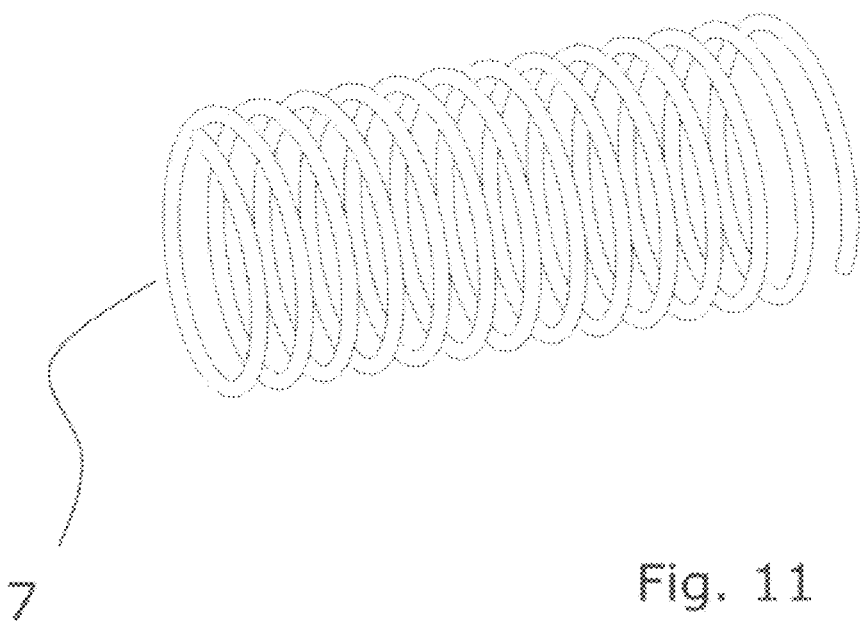
7   Fig. 11
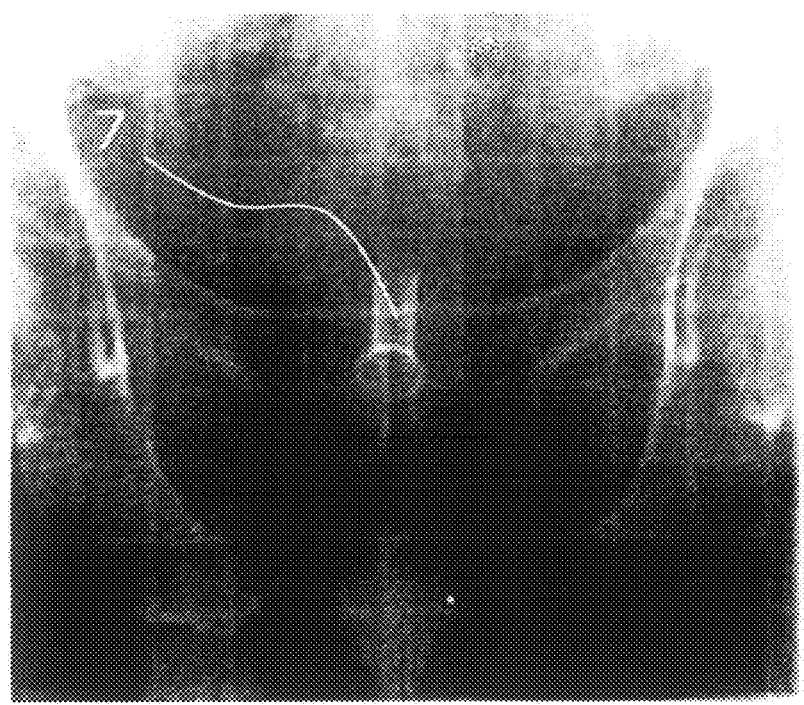
Fig. 12

METHOD OF GUIDING AN IRRADIATION EQUIPMENT

FIELD OF INVENTION

The present invention relates to a method of guiding an irradiation equipment, comprising the step of identifying at least one single, integral three-dimensional element in an image, said at least one single, integral three-dimensional element being positioned in a cavity of a human body or an animal body during the step of identifying. The present invention also relates to a method for identifying a three-dimensional element being positioned in a human body or an animal body in relation to a tissue of interest within the human body or the animal body.

BACKGROUND

In known treatment of cancerous lesions in the human body irradiation of the disordered tissue, such as a tumor, is used in order to destroy the disordered tissue. The disordered tissue may be placed in all parts of the body. When the disordered tissue is positioned in some parts it may be difficult to irradiate without crucially damaging other essential parts of the body and in some cases the irradiation has caused irreversible damage.

In order to avert such damage the irradiation of the disordered tissue is executed by radiating the disordered tissue from different angles, so that the surrounding healthy tissue is only subjected to an irradiation, the effect of which being curable over a short period of time. Thus, the irradiation is not crucially damaging the surrounding healthy tissue. However, the disordered tissue is irradiated from various selected angles in order to destroy it.

Thus, the irradiation of the disordered tissue is restricted by the amount of irradiation, which healthy tissue may tolerate without being crucially or irreversible damaged. This limitation of the irradiation is further increased by the fact that it may be difficult to precisely locate the disordered tissue and to determinate the extension of the disordered tissue inside the body.

U.S. Pat. No. 5,853,366 describes a solution to this problem. The location of the tumor is performed by inserting at least three markers in relevant positions around the periphery of the tumor. These markers are made from stainless steel capable of being detected in a conventional X-ray image of the body in order to position the irradiation source in relation to the tumor before irradiation of the tumor. Each marker is depicted as one point in an X-ray image. These markers are inserted directly into the tissue surrounding the tumor and the markers are barbed or V-shaped in order to securely fasten the markers into the tissue thereby inhibit movement of the markers. Subsequently to positioning of the markers and irradiation of the tumor, the barbed markers have to be removed by invasive surgery.

WO 99/27839 discloses a system for positioning and repositioning of a portion of a patient's body with respect to a treatment or imaging machine including multiple cameras to view the body and the machine. Index markers placed externally on the patient's body, either light-emitting, passive, geometric shapes, or natural landmarks, are identified and located by the cameras in 3D space. Anatomical targets determined from image scanning can be located relative to reference positions associated with the treatment or diagnostic machine. Several forms of camera, index markers, methods and systems accommodate different clinical uses. X-ray imaging of the patient further refines anatomical target positioning relative to the treatment or diagnostic imaging reference point. Movements of the patient based on comparative analysis of imaging determined anatomical targets relative to reference points on treatment or diagnostic apparatus are controlled by the system and process.

WO 02/19908 discloses a method and an apparatus for compensating for breathing and other motions of the patient during treatment, the method comprising: generating images of the target region prior to the treatment; periodically generating positional data about the internal target region based on markers implanted in the patient's body; continuously generating positional data about external motion of the patient's body using one or more external sensors; and generating a correspondence between the position of the internal target region and the external sensors so that the treatment is directed towards the position of the target region of the patient based on the positional data of the external sensors. The target region's position is subsequently matched to the position of the target region in the preoperative images.

WO 02/100485 discloses a system and method for accurately locating and tracking the position of a target, such as a tumor or the like, within a body. In one embodiment, the system includes one or more excitable beacons positioned in or near the target, an external excitation source that remotely excites the beacons to produce an identifiable signal, and a plurality of sensors spaced apart in a known geometry relative to each other. A computer is coupled to the sensors and configured to use the beacon signals to identify a target isocenter within the target. The computer compares the position of the target isocenter with the location of the treatment isocenter. The computer also controls movement of the patient and a patient support device so the target isocenter is coincident with the treatment isocenter before and during radiation therapy.

Even though markers as described above are used to define the extent of the disordered tissue area, the whole area may be difficult to view in the image. For this reason and other reasons when planning the irradiation of the disordered tissue, the medical practitioner or the attending physician plans the irradiation by applying an irradiation margin in order to be sure that all of the disordered tissue area is irradiated. This margin results in some of the healthy tissue being deliberately irradiated and therefore the aforementioned crucial damages may occur. In this respect the irradiation is planned being divided into several irradiation sequences. Also, only fiducial markers are disclosed. A fiducial marker itself provides no possibility of identifying any rotation of the marker. Fiducial markers provide no possibility of localizing the disordered tissue without having at least two, and as disclosed, preferably three fiducial markers employed.

Further reasons for applying the irradiation margin is the inaccuracy in positioning the patient below the irradiation equipment, the inaccuracy of the resolution of the derived image of the disordered tissue and the fact that the internal organs may move over time. Such movement of the internal organs may be caused by respiration and/or by day-to-day movements. The use of implanted markers for guiding the treatment as described above can, to some extend, improve the accuracy of the positioning of the patient.

One method of positioning the patient before treatment is by making an image of the area in which the disordered tissue to be irradiated is located, and the patient is moved in relation to the irradiation equipment by locating the bone structure of the patient in relation to which bone structure the disordered tissue is located in the pre-examination image. The location of bone structure has shown to introduce some of the aforementioned inaccuracy.

Additionally, movement of the disordered tissue to be irradiated between the first pre-examination image and the subsequent image for setting up the irradiation equipment before irradiating the disordered tissue is an indefinable movement. The extent of movement caused by respiration may vary up to 10 cm. The movement caused by respiration varies substantially from one person to another.

Some attempts have been made in order to record the movement caused by the respiration. The movement pattern is entered into the control of the irradiation equipment during the irradiation of the tumor. This additional process of defining a movement pattern is expensive and time consuming, and due to the fact that the respiration of a nervous person, a person suffering from Parkinson's Disease or a person suffering from Cerebral Paralysis is asymptotic, the recorded pattern has often shown to be asynchronous with the present respiration. The recording of a movement pattern may therefore not provide a complete accuracy of the irradiation of the tumor.

An additional solution is known from http://www.elekta.com/healthcareinternational.nsf/pga_Frameset?openpage&url=umc_demonstrates_automatic_marker_detection_with_a-si ("Elekta") disclosing a better detection of the markers using a template of the markers.

Therefore, an improved method of guiding the irradiation equipment is needed in order to at least partly overcome the aforementioned disadvantages of the prior art relating to adjusting the irradiation equipment. An improved method of treating disordered tissue, such as a tumor, may also be needed in order to at least partly overcome the aforementioned disadvantages of the prior art relating to therapy.

U.S. Pat. No. 6,307,914 discloses a moving body pursuit irradiating device comprising a linac for irradiating a medical treatment beam to a tumor, and a tumor marker buried in the vicinity of the tumor, a first X-ray fluoroscope for picking up an image of said tumor marker from a first direction, and a second X-ray fluoroscope for picking up the image of said tumor marker from a second direction at the same time as said first X-ray fluoroscope, first and second recognition processing sections which execute template matching at a real time level at a predetermined frame rate by a shading normalization mutual correlation method for applying a template image of the tumor marker registered in advance to image information digitized by said first and second image input sections, and calculate first and second two-dimensional coordinates of said tumor marker, a central arithmetic processing section for calculating three-dimensional coordinates of said tumor marker from the first and second two-dimensional coordinates calculated by said first and second recognition processing sections; and an irradiating control section for controlling the irradiation of the medical treatment beam of said linac by said calculated three-dimensional coordinates of the tumor marker.

Implanted markers of prior art that is positioned in the body of the patient are buried in the tissue and therefore require invasive surgery to be inserted in the body as well as further subsequent invasive surgery to be retracted from the body.

Diagnostic images made with different imaging technologies and with different medical imaging equipment are derived with a time interval between the images, and with the patient repositioned on a different couch for each image. This results in different set-up conditions for each image. The different set-up conditions result in a difference between the actual position of the tissue of interest inside the body of the patient in the different images, compared to visually clear objects in the images, placed a distance from the tissue of interest, such as bone structures, outer surface of the patient's body etc. The difference between the positions of the tissue of interest in the different images can occur either by internal organ motion inside the patient's body and/or by inaccurate positioning of the patient below the medical imaging equipment.

Therefore, an improved method of collating different images by different medical imaging equipment is needed in order to at least partly overcome the aforementioned disadvantages of the prior art relating to localizing the tissue of interest.

SUMMARY OF THE INVENTION

An objective of the present invention is to provide a method for overcoming the disadvantages and drawbacks of the known methods and systems presented above.

These objectives and the advantages that will become evident from the following description of the invention are obtained by the following embodiments and aspects of the method according to the present invention by providing a method for guiding an irradiation equipment located outside a human body or outside an animal body, the method comprising the steps of:

identifying, in an image, at least one single, integral three-dimensional element visible in the image, said at least one single, integral three-dimensional element being in position in a cavity of the human body or the animal body, establishing, in the image, a preliminary position of the at least one single, integral three-dimensional element visible in the image in relation to a reference, establishing a preliminary position of the irradiation equipment in relation to the reference, adjusting the irradiation equipment in relation to the reference in response to the position of the at least one single, integral three-dimensional element in relation to the reference.

During the step of identifying, in an image, at least one single, integral three-dimensional element visible in the image, the at least one single, integral three-dimensional element is in position. Prior to identifying, in an image, at least one single, integral three-dimensional element visible in the image, an additional step may be inserting the at least one single, integral three-dimensional element into a cavity of the human body or the animal body.

By identifying the position of the at least one single, integral three-dimensional element in relation to the position of the disordered tissue, the position of the disordered tissue may then be established based on establishing the position of the three-dimensional element. This is advantageous due to the fact that the disordered tissue is not identifiable in all kinds of images, in which the three-dimensional element is identifiable. By being able to establish the position of the three-dimensional element in a two dimensional image, the exact position of the disordered tissue may be established due to the fact that the element and the disordered tissue moves simultaneously in relation to the human or animal body.

The dimensions of the three-dimensional element are known in advance and based on the two-dimensional image of the three-dimensional element the dimensions give an exact knowledge of how the three-dimensional element is positioned inside the body and perhaps is being rotated inside the body. By knowing the dimensions of the three-dimensional element in advance and by being able to detect the dimensions in an image, the exact position of the three-dimensional element inside the body may be calculated. The knowledge about the position of the three-dimensional element established in the image gives an exact knowledge of where the disordered tissue is positioned, because the disordered tissue and the three-dimensional element have been found to have a substantially fixed relationship and any possible movements of the disordered tissue results in corresponding movements of the three-dimensional element and vice versa.

Hereby the object is obtained of the positioning of the disordered tissue being performed accurately based on the position of the element even though the patient has been moved between the examination room and the irradiation room or has moved just before setting up the patient for irradiation. It is likewise possible during the irradiation of the patient to adjust the equipment so that the element and thereby the disordered tissue, such as a tumor, of the patient stays in focus of the irradiation equipment.

By being able to adjust the irradiation equipment based on the element, the irradiation may be performed more precisely and the adjusting of the irradiation equipment may be done automatically by a computer.

Additionally, by being able to irradiate more precisely, it is possible to subject the patient to a higher total dose of irradiation without damaging tissue surrounding the disordered tissue and as a result it is possible to subject the patient to irradiation more times with the same refractory dose in order to more effectively eliminate the disordered tissue.

Additionally, the method may according to the present invention further comprise the steps of:
  monitoring a possible movement of the three-dimensional element in relation to the irradiation equipment,
  adjusting the irradiation equipment in response to the possible movement of the three-dimensional element.

Hereby the object is obtained of the aforementioned inaccuracies are increasingly diminished in that the possible movements of the body and/or of the element is equalized by adjusting the irradiation equipment in response to the possible movement of the at least one single, integral three-dimensional element. It is likewise possible during the irradiation to adjust the equipment so that the three-dimensional element and thereby the disordered tissue, such as a tumor, of the patient stays in focus of the irradiation equipment. Furthermore, the adjustment of the irradiation equipment may be an adjustment of the position of the irradiation equipment, of the couch on which the patient is placed, of the power of the irradiation source, of the focal point of the beam, of the intensity of the irradiation beam, of movement of plates or a shield changing the shape of the irradiation beam, and so forth.

Additionally, the adjusting of the irradiation equipment may furthermore be a deflection or a focusing of the irradiation beam in relation to any displacements during irradiation. Such displacement may be a forced displacement, such as a tilting or a partial rotation of the patient during irradiation. The displacement may also be a voluntary or involuntary displacement by the patient. The voluntary displacement may be the patient moving on the couch or walking around in the irradiation room and the involuntary displacement may be movements due to motoric diseases such as Parkinson's Disease or Cerebral Palsy.

The advantages of being able to adjust the irradiation equipment during irradiation reside in the possibility of irradiating the body from different angles. Thereby, the disadvantage of irradiating possibly healthy tissue surrounding the disordered tissue is minimized. Furthermore, the adjustment may be performed so that irradiation of certain critical healthy tissue is avoided. The adjustment of the irradiation equipment may also be a limitation of the total dose of irradiation from a certain angle in order to avoid exceeding the irradiation limit of healthy tissue being irradiated from that certain angle.

The steps of identifying, establishing, monitoring and adjusting may be done automatically, and the monitoring step may be executed at an appropriate frequency, such as once every 3 seconds or less depending on the equipment available.

In another aspect of the present invention the reference is a previous image of the three-dimensional element having been inserted into the cavity of the body. Such a previous image may conveniently be the image in which the disordered tissue, such as a tumor 6, was detected and the dimensions of the disordered tissue were established during a pre-examination of the patient.

In yet another aspect of the present invention the previous image of the at least one single, integral three-dimensional element may also be the last image derived of the three-dimensional element or the image derived for setting up the patient before irradiation.

According to the present invention at least a part of the at least one single, integral three-dimensional element may have a shape allowing passage of a liquid, a gas or solids inside the cavity. Hereby the natural flow of liquid, gas, solid inside the cavity is maintained, such as urine in the urethra and blood in the vein, or such as intestinal gas in the intestines and breath in the trachea or in the lungs, or such as solid faeces in the intestines, even though the irradiation may cause some swelling of the tissue surrounding the cavity.

Additionally, at least a part of the at least one single, integral three-dimensional element may, according to the invention, be expandable towards the cavity from inside the cavity, when being released in the cavity. Likewise, the natural flow of liquid, gas or solid is maintained inside the cavity, such as urine in the urethra and blood in the vein, or such as intestinal gas in the intestines and breath in the trachea or in the lungs, or such as solid faeces in the intestines, even though the irradiation may cause some swelling of the tissue surrounding the cavity.

Furthermore, by expanding the cavity into which the at least one single, integral three-dimensional element is positioned, the three-dimensional element is firmly positioned inside the cavity without moving inside the cavity. Any other fastening means such as a barbed shape of the three-dimensional element is dispensable, and the element is easily removed without damaging the inside of the cavity.

In one aspect of the present invention, the at least one single, integral three-dimensional element may have a tubular shape allowing liquid, gas or solid inside the cavity of the body to flow freely. This tubular shape will maintain holding the cavity open also during the irradiation and the possible resulting subsequent swelling.

Additionally, when inserting of the three-dimensional element is an aspect of the present invention, inserting of the three-dimensional element may be performed through a natural opening of the body without at all or at least without substantially penetrating any tissue of the body. This way of inserting a three-dimensional element as a marker does not acquire invasive surgery, and thereby the risks related to such surgery is eliminated or at least minimized.

Furthermore, the method may according to an additional aspect of the present invention comprise the step of retracting the three-dimensional element through a natural opening of the body without at all or at least without substantially penetrating any tissue of the body. By retracting the three-dimensional element through the natural cavity or opening, the removal of the three-dimensional element is performed without invasive surgery and the risks of contamination related to such surgery is eliminated or at least minimized.

The three-dimensional element is inserted into a natural cavity and is therefore not damaging the surrounding tissue because the cavity is a natural opening of the body. The element is therefore not penetrating any tissue in order to be fastened inside the body. The three-dimensional element is fastened by at least partly abutting the inside of the cavity in order for the three-dimensional element not to move inside the cavity.

Advantageously, the step of monitoring and adjusting may, according to another aspect of the invention, is performed during irradiation of the disordered tissue such as the tumor.

In another aspect of the present invention the at least one single, integral three-dimensional element may be substantially tubular endoluminal prosthesis. The three-dimensional element may therefore already be positioned inside the body for another purpose such as for expanding a diminished urethra or ureter. The three-dimensional element will maintain holding the cavity open, also during the irradiation and the possible resulting subsequent swelling caused by the irradiation. The three-dimensional element is capable of staying in the cavity during a period of at least 30 days and is therefore capable of keeping the cavity open to permeation of liquids, gases or solids all during the irradiation even though the irradiation is divided into periods of hours, days or weeks.

In respect of the at least one single, integral three-dimensional element being a substantially tubular endoluminal prosthesis, the three-dimensional element reduces the need for any additional catheters in order to hold the cavity in which the three-dimensional element is inserted open to permeation of liquids, gases or solids.

The at least one single, integral three-dimensional element may in yet another aspect of the present invention be a helically coil of at least one wire. Hereby it is obtained that retraction of the three-dimensional element is possible through the natural cavity or opening through which it was inserted by pulling the wire.

Advantageously, the at least one single, integral three-dimensional element may, according to an aspect of the invention, be of a biologically compatible material, such as polymers, biological material or metal, such as stainless steel, titanium, platinum, palladium, nickel-titanium and other alloys or combinations of any of these materials. By applying a three-dimensional element of such a biologically compatible material the three-dimensional element does not cause an infection when being in the cavity of the human or animal body.

Furthermore, the at least one single, integral three-dimensional element may according to an additional aspect of the present invention be made of a shape memory alloy. By applying a shape memory alloy the three-dimensional element is capable of expanding within the cavity.

In another aspect of the present invention the at least one single, integral three-dimensional element may be made of a shape memory alloy having a transition temperature above body temperature, preferably between 37° C. and 50° C.

Body temperature is construed as the temperature of the body of the human or of the animal during the application of the method according to the invention. In most applications of the method, the body temperature of a human will be around 37° C.

The body temperature may however differentiate depending on whether it is a human body or an animal body. Some animals have lower normal body temperature than humans, and some animals have higher normal body temperature than humans.

Also, the body temperature may differentiate depending on the physical state of the human or the animal. The temperature may be higher due to fewer if the human or the animal is suffering from illness causing fewer, and the body temperature may be lower due to perhaps unstable blood flow, if the human or animal is newborn or is elderly, or if the human or the animal is suffering from illness causing the unstable blood flow.

By applying a shape memory alloy the three-dimensional element is capable of expanding within the cavity when heated to the transition temperature. Provided the transition temperature is about the normal body temperature of the human or animal body, the expanding is performed when the body has warmed up the element and this expansion of the three-dimensional element is performed without additional applying of heat. In the case of a transition temperature in range above the body temperature the expanding is obtainable by heating the three-dimensional element e.g. by flushing of sterile water or the like fluids, having a temperature above the transition temperature.

By using shape memory alloy having a transition temperature between 37° C. and 50° C., the surroundings inside the body is not scalded, which otherwise may give rise to an infection or to damaged tissue.

The at least one single, integral three-dimensional element may, in another embodiment of the present invention, be made of a material being plastically deformable by hand at a temperature below 37° C., preferably under 20° C. and above 5° C. By using a material being plastically deformable by hand the three-dimensional element may be easily retracted by the manual force of a physician, and the three-dimensional element may easily be deformed to a smaller size during the retraction of the three-dimensional element.

Additionally, the step of monitoring the movement of the at least one single, integral three-dimensional element may according to the present invention be performed by producing up to 50 images per second, at least 2-50 images per second, at least 1 image per second, at least 12 images per minute or at least 2 images per minute depending on the medical imaging equipment, at least 2-50 images per second, at least 1 image per second, at least 12 images per minute or at least 2 images per minute.

By sampling as frequently as described, the possible movement of the three-dimensional element and thus of the disordered tissue may be equalized almost instantly and the method is performed almost continuously, whereby the aforementioned damage of healthy tissue is substantially decreased.

According to the present invention, the image may be a two dimensional projection image or a three-dimensional image, and wherein the image is derived and processed by medical imaging equipment.

Said medical imaging equipment may according to the present invention be Magnetic Resonance scan (MR-scan), Nuclear Magnetic Resonance scan (NMR-scan), Magnetic Resonance Image scan (MRI-scan), Computerized Tomography scan (CT-scan), Cone Beam CT-scan, Positron Emission Tomography (PET), Single Positron Emission Computed Tomography (SPECT), Single Positron Emission Tomography (SPET), Image-Guided-Radiation-Therapy (IGRT), Ultrasound-scan, or X-ray, high-energy photons equipment or high voltage equipment.

The image may also, according to the invention, be derived and processed by utilizing energy of the irradiation source. Thereby use of other equipment is no longer necessary and a substantial amount of cost and space in the irradiation room is saved.

In an additional aspect of the invention, the image may be derived and processed by utilizing energy of the irradiation beam. Thus, use of other equipment is no longer necessary and a substantial amount of cost and space in the irradiation room is saved.

Furthermore, the patient is not unnecessarily irradiated. When the dose of irradiation is calculated, the irradiation of the patient, in order to produce images to establish the extension of the disordered tissue, such as a tumor 6, is included. The dose is calculated so that the surrounding healthy tissue is not un-recoverably damaged. The irradiation of the patient is thereby used in order to treat the patient in the correct area and not just for producing examining images.

By using the same equipment as for the irradiation of the disordered tissue, time is saved for changing equipment back and forth when an image has to be derived.

In another embodiment of the invention, the image may be derived and processed by utilizing electric energy from an energy source for producing electric power for the irradiation source.

Furthermore, the at least one single, integral three-dimensional element may, according to an aspect of the invention, have a design enabling insertion and/or retraction of the three-dimensional element with conventional endoscopic equipment. By being able to use conventional endoscopic equipment during insertion and/or retraction of the three-dimensional element, costs of additional equipment is saved and the time in changing between utilizations of different equipment during the insertion or retraction of the three-dimensional element is decreased.

The cavity may have at least one surrounding wall, and the at least one single, integral three-dimensional element may, according the invention, have a collapsible design when inserting the three-dimensional element, and said three-dimensional element design being expandable towards the surrounding wall of the cavity, when being released in the cavity. The collapsible design reduces the impact on the inside wall of the natural cavity through which the insertion takes place. When being in the collapsed state, the element may have a substantially two-dimensional extension, and when being in the expanded state, the element will change from the possibly two-dimensional extension to the three-dimensional extension.

Advantageously, the reference may, according to the present invention, be located in a position inside or in a position outside the human body or the animal body.

In addition, the reference may, according to the invention, be a bone structure.

Furthermore, the reference may, according to an aspect of the present invention, be an image-detectable object.

The present invention also relates to an apparatus for carrying out the method according to any of the aforementioned methods, said apparatus comprising means for identifying the three-dimensional element, means for establishing a preliminary position of the three-dimensional element and the irradiation equipment, means for monitoring a possible movement of the element and means for adjusting the irradiation equipment or the human body or the animal body in response to the movement.

The means for identifying the three-dimensional element may, in one aspect, be a computer program for image-detection and means for establishing a preliminary position of the three-dimensional element may also be a computer program for image-detection. The irradiation equipment may be any conventional irradiation equipment for irradiating disordered tissue, such as a tumor. Means for monitoring a possible movement of the element may be a computer transmitting signals to the means for adjusting the irradiation equipment or the human body or the animal body in response to the movement.

According to an aspect of the invention, the invention relates to a method for identifying a three-dimensional element, said three-dimensional element being positioned in a human body or an animal body in relation to a tissue of interest within the human body or the animal body, the method comprising the steps of:

identifying in a first image the three-dimensional element, visible in the first image, and wherein the first image is derived and processed by a first type of medical imaging equipment, identifying in a second image the three-dimensional element, visible in the second image, and wherein the second image is derived and processed by a second type of medical imaging equipment, collating the first image and the second image based on a determination of the position of the three-dimensional element in the first image and of the position of the three-dimensional element in the second image.

A combination of different images, generated by different imaging technologies is used during the planning of radiation therapy. During the planning of radiation therapy, the tissue of interest, such as a cancerous tumor, is identified in diagnostic images. Hereafter position and shape of the tumor is localised and a profile of the irradiation therapy to be given to the patient is generated, based on the shape and position of the tumor.

Any inaccuracy of the identification of the tumor during the planning of radiation therapy will result in inaccurate irradiation during the treatment, resulting in a risk that the irradiation does not hit the intended tissue of interest. Possibly, it may result in traumatic irradiation of healthy tissue and/or it may result in part of the unhealthy tissue not being irradiated.

By deriving at least a first image and a second image, and by collating the images by determining the position of the three-dimensional element, the three-dimensional element and hereby the tissue of interest will be identically positioned in the images. Thereby, the possible advantages of the first type of medical imaging equipment and the possible other or additional advantages of the second type of medical imaging equipment will be obtained at the one and same time in respect of the mutual positional relationship between the three-dimensional element and the tissue of interest.

By using a three-dimensional element as marker being positioned inside, or at least in close vicinity of the tissue of interest, the images can be collated very accurately near the marker, and hereby near the tissue of interest. Hereby it is possible to collate the images accurately based on the position, in the images, of the three-dimensional element, hereby ensuring that the position of the tissue of interest, being positioned in an accurate position in relation the three-dimensional element, is also determined accurately in the images.

Given the more accurate determination of the position of the tissue of interest in the different images of the different medical imaging equipment, a physicist and/or medical personnel will be able to identify and localise the tissue of interest, such as a cancerous tumor, very accurately.

Contrary hereto, when trying to compare images that are derived by different medical imaging equipment, according to prior art methods, the mutual positional relationship between the marker and the tissue of interest is not possible to establish accurately due to the fact of the marker, either not being present in the human or animal body, or the marker not being positioned in a position ensuring a constant mutual relationship between the position of the marker and the position of the tissue of interest.

By using a marker that is a three-dimensional element, such as a tubular, endoluminal prosthesis, the collation of the different images of the different medical imaging equipment can be guided by an automatic detection of the three-dimensional element in the different images derived by the different types of medical imaging equipment, hereby making it possible to automatically guide the collation of the position, in the different images, of the three-dimensional element and thus of the tissue of interest.

The three-dimensional element as a marker and being intended for guiding the irradiation equipment, can also be used for collating two or more diagnostic images used for identification, localisation and generation of irradiation profile generated during the planning of the radiation therapy. Use of the same three-dimensional element for both guiding an irradiation equipment and for collating of images for planning of the radiation therapy is feasible without any need for reinsertion or repositioning of the three-dimensional element.

The three-dimensional element may have different geometrical properties depending on the actual intended position of the three-dimensional element in the human or animal body. Additionally or alternatively, the three-dimensional element may have different physical properties depending on the actual intended use of the three-dimensional element in the human or animal body, apart from the use as a marker in different images. Possibilities of geometrical and physical properties are mentioned in the following:

Thus, the three-dimensional element may have a shape allowing passage of a liquid, gas or solid inside the cavity in which the three-dimensional element is positioned. The three-dimensional element may be expandable towards the cavity from inside the cavity, when released in the cavity. The three-dimensional element may have a tubular shape allowing passage of a liquid, gas or solid inside the cavity in which the three-dimensional element is positioned. The three-dimensional element may be a tubular endoluminal prosthesis, possibly made of a helical coil of at least one wire.

The three-dimensional element may have a design enabling insertion and/or retraction of the three-dimensional element with conventional endoscopic equipment. The three-dimensional element may have a collapsible design, enabling a collapsed design when inserting the three-dimensional element in a cavity of the human or animal body, and enabling an expanded design when the three-dimensional element has been positioned in the cavity of the human or animal body.

The three-dimensional element may be made of a biologically compatible material, such as polymers, biological material or metal, such as stainless steel, titanium, platinum, palladium, nickel-titanium and other alloys or combinations of any of these materials.

The three-dimensional element may be made of a shape memory alloy having a transition temperature with a one-way-memory effect at a temperature above body temperature, preferably at a temperature between 37° C. and 50° C. Alternatively or additionally, the three-dimensional element may be made of a material being plastically deformable by hand at a temperature below body temperature, preferably at a temperature below 37° C., more preferred at a temperature below 20° C. and above 5° C. Even in the alternative, the three-dimensional element may be made of a shape memory alloy being super elastic at body temperature, preferably being super elastic at 37° C.

The medical imaging equipment according to the aspect of the invention may be any one of the following imaging equipment: Magnetic Resonance scan (MR-scan), Nuclear Magnetic Resonance scan (NMR-scan), Magnetic Resonance Image scan (MRI-scan), Computerized Tomography scan (CT-scan), Cone Beam CT-scan, Positron Emission Tomography (PET), Single Positron Emission Computed Tomography (SPECT), Single Positron Emission Tomography (SPET), Image-Guided-Radiation-Therapy (IGRT), Ultrasound-scan, or X-ray, high-energy photons equipment or high voltage equipment. The image may be derived and processed by utilizing energy of the irradiation equipment, or the image may be derived and processed by utilizing energy from the treatment irradiation beam.

BRIEF DESCRIPTION OF THE DRAWINGS

In the following, the present invention will be described with reference to the accompanying drawings, in which:

FIGS. 9, 10 and 11 show other examples of a three-dimensional element, FIGS. 12 and 13 show an example of three-dimensional element in an image derived from a mega voltage equipment.

The drawings are schematically and shown for the purpose of illustration.

Figure 1:
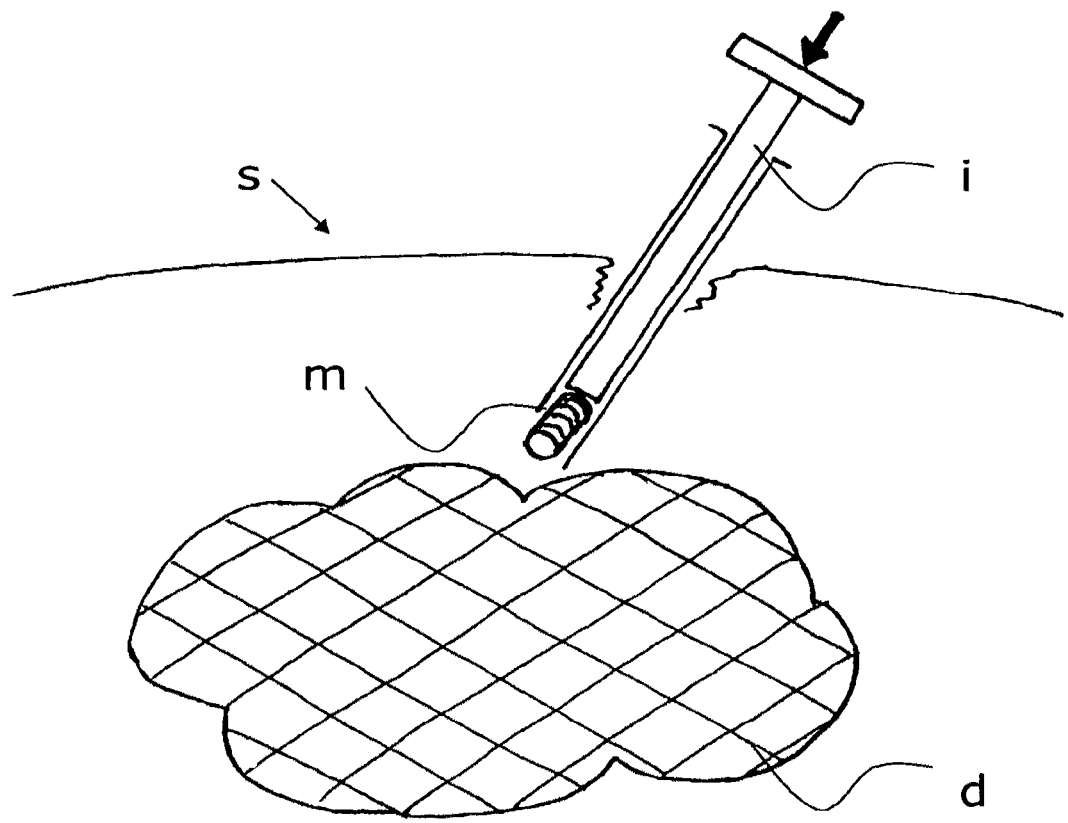
FIG. 1 shows a prior art marker being inserted by surgery through the tissue of a human body.
Figure 2:
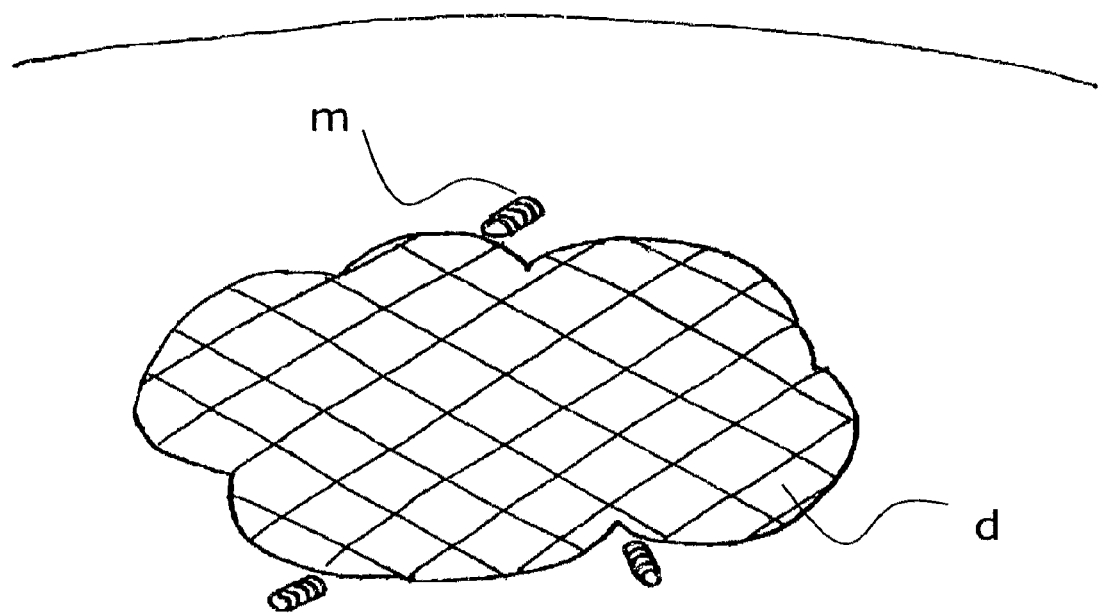
FIG. 2 shows three prior art marker which has been inserted into the tissue surrounding a tumor.

FIG. 1 shows the insertion of prior art markers m through the skin i by use of invasive surgery, the insertion being done in order to locate the disordered tissue d, such as a tumor, in an image derived for positioning the irradiation of the tumor d. When inserted as shown in FIG. 2, the three or more markers m are positioned in relation to the irradiation equipment, and the irradiation source is turned on for a period of time. Subsequently to the time period of irradiation, the irradiation is interrupted. The irradiation of the tumor d may be continued when a period of at least a few days has lapsed so that the surrounding healthy tissue may withstand a new irradiation. During the time period of irradiation, the irradiation equipment is at no time adjusted in order to compensate for any movement of the tumor during this irradiation.

The prior art markers m shown FIGS. 1 and 2 may move considerably within the body between two irradiation periods in which case more markers may have to be inserted.

DESCRIPTION OF THE PRESENT INVENTION

Figure 3:
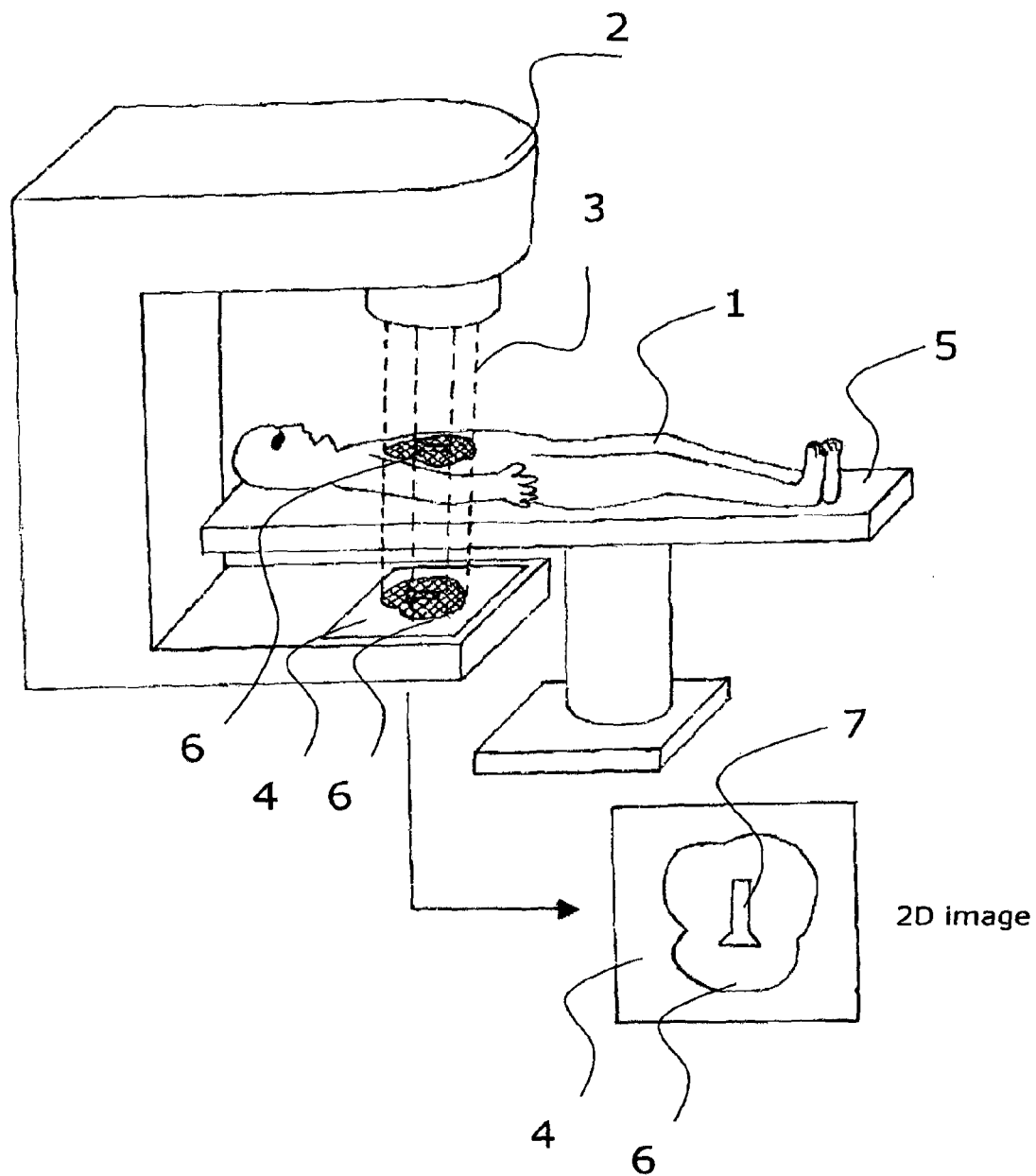
FIG. 3 shows a human body lying on a couch below an irradiation equipment.
Figure 4:
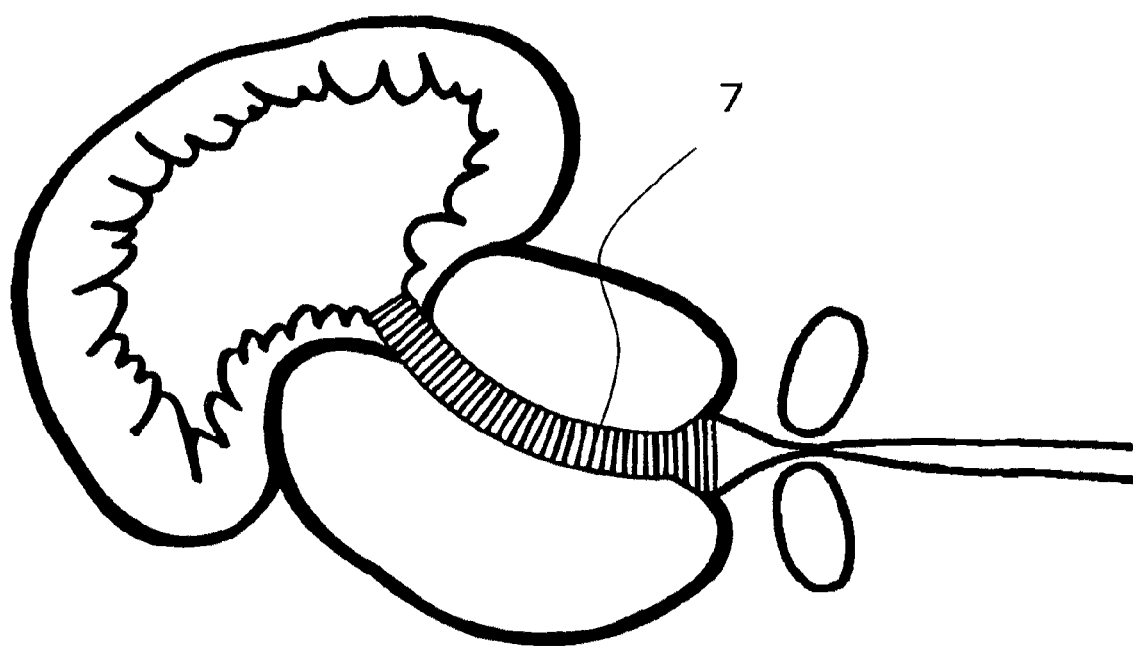
FIG. 4 shows a three-dimensional element having been inserted into the natural cavity a urethra of a male.
Figure 5:
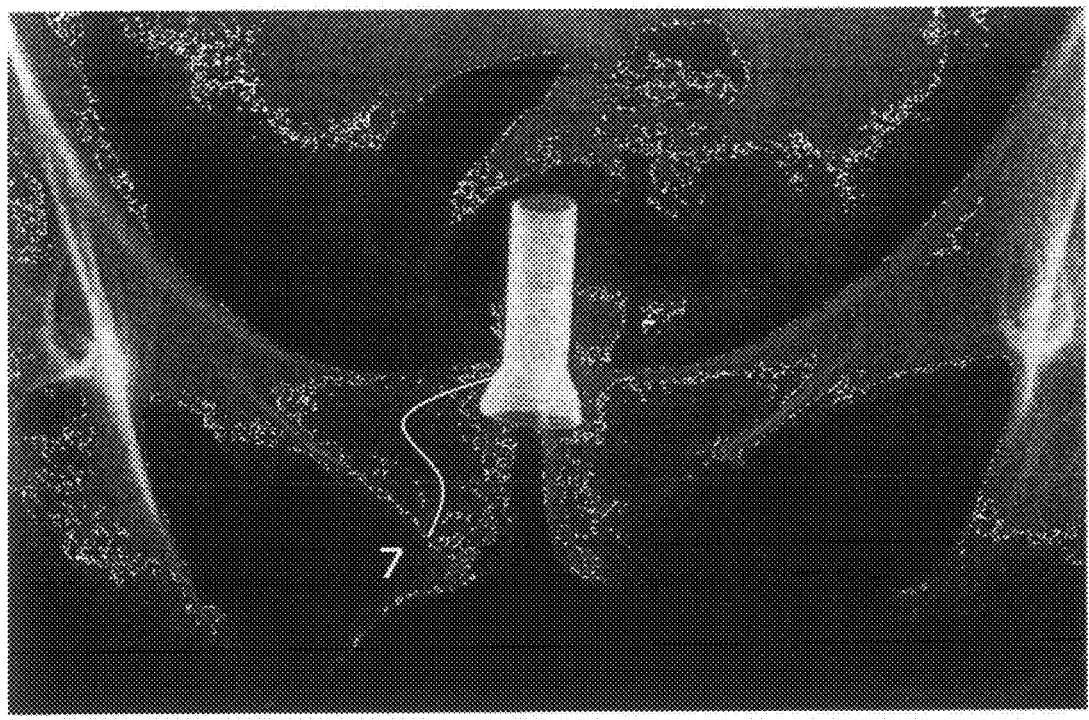
FIG. 5 shows an X-ray image of a three-dimensional element as shown in FIG. 4.
Figure 6:
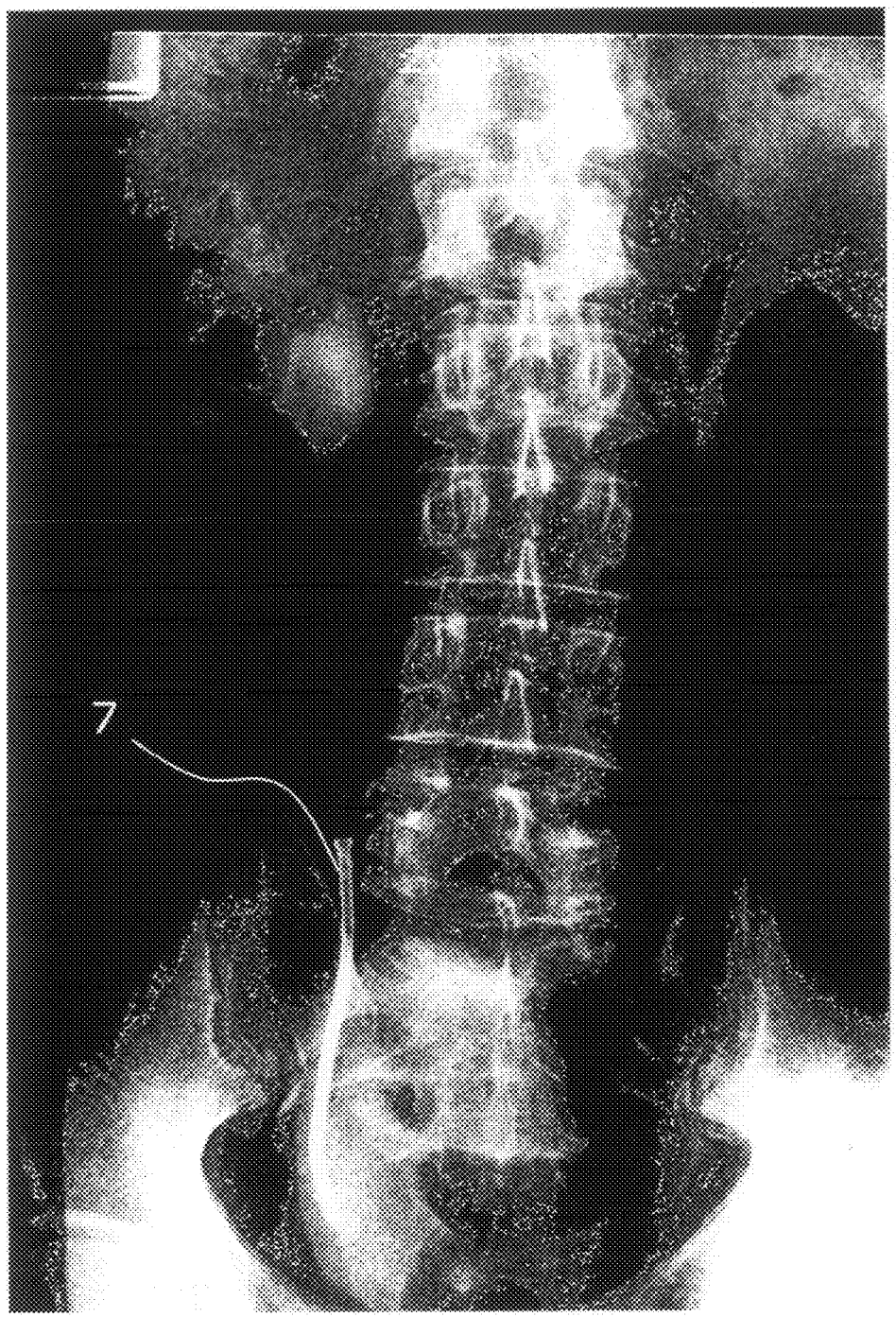
FIG. 6 shows an X-ray image of another three-dimensional element.

When a patient 1 has been given the prognosis of having cancer, the cancer is often positioned inside the body of the patient in the form of disordered tissue 6, such as a tumor 6, as shown in FIG. 3. The prognosis is often given by a medical practitioner or an attending physician who has derived an X-ray image 4 or the like image 4 of the patient 1. The image 4 is investigated, and the tumor 6 is located in the image 4 before the actual treatment of the patient 1, as example by irradiation of the tumor 6. In the following, a tumor 6 will be used as an example of disordered tissue. However, other types of disordered tissue, other than tumors, may also be treated during guiding of the irradiation equipment when employing the equipment guidance method according to the invention A series of images 4 are derived in order to establish the extension of the tumor 6. In one aspect of the present invention, the position of the three-dimensional element 7 is determined by producing a series of images 4 using as an example MR-scanning techniques. When establishing the extent of the tumor and if no element is already positioned in the body of the patient 1, a three-dimensional element 7, being suitable as a marker of the tumor 6, is inserted into the patient 1. In other situations, when establishing the extent of the tumor, an element, being suitable as a marker of the tumor 6, is already positioned in the body of the patient 1. The three-dimensional element is inserted or is in position within a certain distance from the tumor 6 to be treated or inside the volume to be treated. When irradiating a tumor 6 inside the prostate, the three-dimensional element 7 is often positioned inside the urethra inside the prostate and therefore in immediate vicinity of the area 6 to be treated as shown in FIGS. 4, 5, 6, 7, 12, 13 and 14.

In one aspect of the present invention, the three-dimensional element 7 is identified automatically and a preliminary position is established in relation to a reference. The reference may, according to one embodiment of the present invention, be set for example as a point in the middle of the three-dimensional element 7.

As mentioned, the position of the three-dimensional element 7 is determined by producing a series of images 4. The images 4 are entered into the computer. The computer calculates and saves the mutual relationship between the three-dimensional element 7 and the tumor. The mutual relationship has been derived by establishing a distance between the tumor 6 and the three-dimensional element 7, which distance is fixed during any kinds of movements of tissue inside the body in relation to for example the bone structure or movements of the body 1 as a whole. By the wording a fixed distance is meant that the tumor 6 and the three-dimensional element 7 have substantially no relative movement in relation to one another.

Establishing a preliminary position of the three-dimensional element 7 in the image 4 in relation to a reference may, according to the invention, be performed by identifying a known geometrical shape, such as the pitch distance between the windings of a coil shaped element 7, the bending in a structural transition of the three-dimensional element 7, a circumference or contour of the three-dimensional element 7, etc.

Subsequently, a preliminary position of the irradiation equipment 2 is automatically established by a computer. Establishing a preliminary position of the irradiation equipment 2 in relation to the reference may be performed by measuring the distance from the position, where radiation is emitted from the irradiation equipment and to starting point/set-up point in the image 4, including identifying a level in which the plane of the image 4 is positioned. Establishing of a preliminary position of the irradiation equipment in relation to the reference may also be performed by identifying where a certain bone structure in the body is positioned in relation to the irradiation head or it may be performed by establishing the mutual relationship between the couch and the position where the radiation is emitted form the irradiation equipment.

During the period of time in which the irradiation equipment 2 is activated in order to irradiate the tumor 6, any possible movement of the element 7 is monitored. Provided a possible movement is being detected the irradiation equipment 2 is adjusted in response to the movement of the element so that the irradiation of the tumor 6 is executed as precisely as possible.

In this regard, the irradiation equipment 2 comprises, among other features, the couch where the patient may lie or sit, the irradiation source, the irradiation beam, and plates or shield defining the shape of the beam.

Adjusting the irradiation equipment 2 may therefore according to the invention be an adjustment of the position of the irradiation equipment 2, an adjustment of the position of the couch 5 in relation to the equipment 2, an adjustment of the power of the irradiation source, an adjustment of the focal point of the beam 3, an adjustment of the intensity of the beam 3, an adjustment of movement of the plates or the shield in order of changing the shape of the beam 3 and so forth. The adjusting of the irradiation equipment 2 may furthermore be a deflection of the irradiation beam 3 in relation to a body to be irradiated.

The adjustment of the irradiation equipment 2 may also be to turn down the power of the irradiation source, when the element 7 is monitored to be outside a certain area, and to turn on the power again, when the element 7 is within the certain area again. It may furthermore be possible to adjust the irradiation power during the irradiation period, in order to subject some areas of the tumor 6, to higher dose of irradiation than other areas, e.g. subjecting the irradiation margin area to smaller dose of irradiation than the tumor 6 itself, or subjecting some very critical areas in the human or animal body to smaller dose of irradiation than the tumor 6 itself.

Instead of turning on or turning down the power, the irradiation beam may be deflected or the focal point of the irradiation beam may be changed. By irradiating the whole area of the tumor 6 it may be necessary to irradiate the tumor 6 by moving the irradiation beam in a predefined movement pattern.

Monitoring a possible movement of the three-dimensional element 7 in relation to the irradiation equipment 2 may be performed in pre-selected intervals such as 10-20 times a second, such as 1-2 per minute, etc. depending on the medical imaging equipment and based on the expected frequency of movement of the three-dimensional element 7.

When planning irradiation of the patient, an irradiation margin is used in order to be certain that the tumor 6 is irradiated sufficiently, even though the step of monitoring and of adjusting provides for a decrease of the size of the irradiation margin.

Before performing the actual irradiation, the three-dimensional element 7 having been positioned in relation to the tumor 6 is located when the patient is lying on the irradiation couch or when the patient in any other way is located in the irradiation room. The location of the three-dimensional element 7 may in one embodiment be established by deriving a high-voltage image 4 using the irradiation equipment 2 itself. The patient or the irradiation equipment 2 is positioned so that the three-dimensional element 7 is positioned as previously planned, and so that the reference is centered in the middle of the three-dimensional element 7. Hereby a starting point is established also called the preliminary position of the irradiation equipment 2 and of the element 7 in relation to the reference.

The reference may in this aspect be any previous image 4 derived identifying the tumor 6 in relation to the three-dimensional element 7. The previous image 4 may also be the last image 4 derived in order to monitor a possible movement of the three-dimensional element 7, or the reference may be an image 4 derived during the pre-examination. By the previous image 4 is meant an image 4 derived before the present image 4, in which previous image 4 the position of the three-dimensional element 7 has been established.

In another aspect of the present invention the reference may be the couch on which the patient is located during the irradiation or the reference may be the irradiation equipment 2 itself. The reference may also be a certain bone structure or another identifiable structure inside or outside the human or animal body.

By automatically monitoring and detecting a possible movement of the three-dimensional element 7, the method according to the present invention is capable of adjusting the irradiation equipment 2 or the patient in relation to each other every time the three-dimensional element 7 is moving from the established preliminary position. It is hereby obtained to compensate for frequent movement of the tumor caused for example by respiration or small movements made by the patient, said movements being made by force, being made voluntary by the patient or being made involuntary by the patient. A considerable improvement of the accuracy of the irradiation is accomplished and the irradiation of healthy tissue is reduced.

Figure 14:
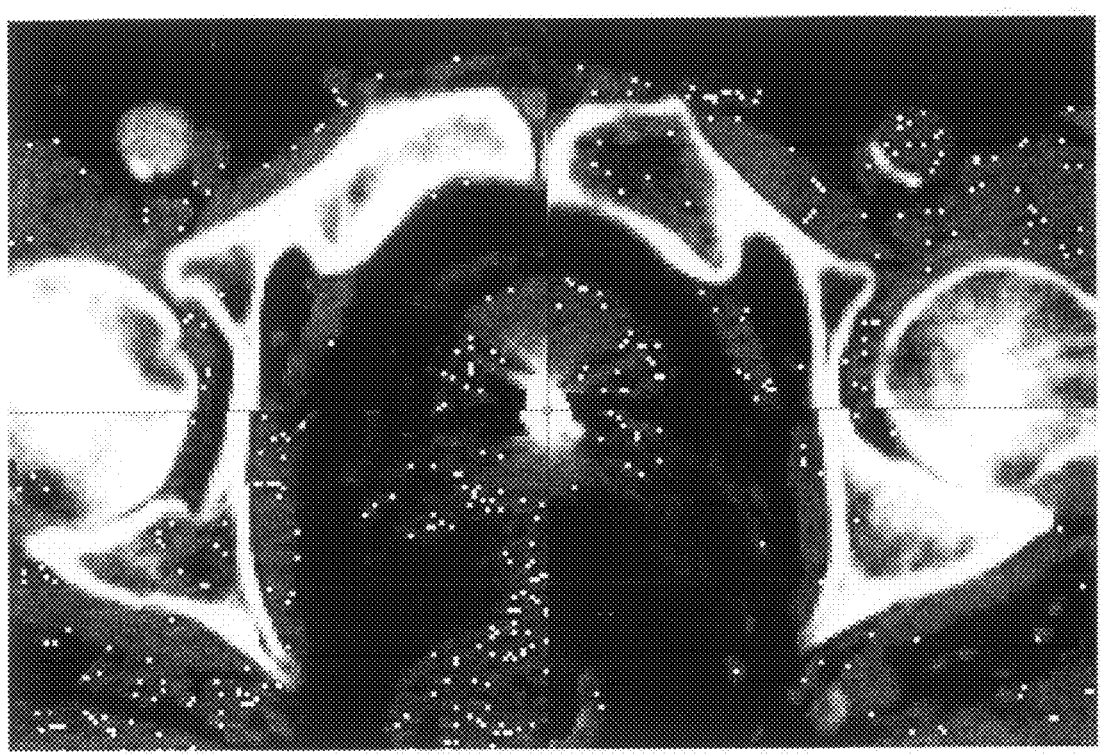
FIG. 14 shows an amalgamation of images having the three-dimensional element in the center and derived by CT-scan.

FIG. 14 shows that merging different images 4 together based on a center of the images being positioned within boundaries of the three-dimensional element 7 gives a very accurate localization of the tissue of interest, for example the prostate.

By sampling images 4 during the irradiation of the tumor the monitoring of any possible movement of the three-dimensional element 7 and thus of the tumor 6 may be equalized momentarily all most the instance the movement appears. The sampling frequency may vary from ten images per second or faster to one image per three second depending on the equipment used for producing the images 4.

High voltage equipment such as the irradiation equipment 2 itself has a sampling frequency (or sampling rate) less than for example MR-scanning equipment. However, when using the irradiation equipment 2 itself the other equipment is dispensable.

Often, X-ray is used to establish the first image 4 for localization of the tumor 6 in relation to the three-dimensional element 7, but other equipment such as CT-scanning equipment and MR-scanning equipment may be used likewise. The position of the tumor 6 in relation to the three-dimensional element 7 is thus determined prior to the patient entering the irradiation room.

In one aspect of the present invention the patient itself inputs the first image 4 into the computer of the irradiation equipment, said first image 4 being relied upon as the previous image 4 and thereby as the reference in the computer of the irradiation equipment 2. Subsequently, the computer controls the irradiation equipment 2 for producing an image 4 for establishing the position of the element 7 in relation to the irradiation equipment 2. Then the computer adjusts the irradiation equipment 2 if necessary in relation to the position of the element 7 and the irradiation of the human or animal body begins.

The three-dimensional element 7 may be all kinds of objects provided in the body for a number of other reasons. Such objects may be all kinds of endoluminal prosthesis often being tubular, such as a element 7 placed in the urethra and other natural cavities, such as the urological tract, the urethra, the biliary tract, the airways, the intestine, or the blood vessels in the human body.

If an element 7 is already present in the vicinity of the tumor to be irradiated, the element 7 will secure the passage of the liquid, gas or solid inside that natural cavity, as mentioned above. It is well known that the tissue having been irradiated becomes distended and thereby may cause a reduction of the volume of the natural cavities. A three-dimensional element 7, such as a tubular endoluminal prosthesis can help to counteract this reduction of the volume of the cavity.

For the reason of avoiding a reduction of the volume of the natural cavities one or more elements 7 may be provided which may be used in guiding the irradiation equipment 2 in order to adjust for the aforementioned momentary movements during the irradiation. Furthermore the three-dimensional element 7 may in another aspect of the present invention have a shape enabling insertion and retraction in a natural cavity. Additionally, when inserted into the cavity a part of the element 7 may expand in order to provide a force against the surrounding wall of the cavity so as to fasten the element 7 in this position. In other embodiments of the present invention the fastening of the element 7 in relation to the surrounding walls of the cavities may be done by at least a part of the element 7 being attached at least partly to tissue outside the natural cavity or by the element 7 having an Y-shape, an I-shape or the like shapes processing a locking mechanism blocking movements in the longitudinal direction of the cavity, such as the ureter, vein or the like cavity.

An example of such a three-dimensional element 7 according to the present invention is a tubular stent used for insertion into the urethra in the vicinity of the prostate as shown in FIGS. 4, 5, 7 and 8. When the stent has been positioned in the part of the male urethra passing through the prostate and expansion of the end of the element 7 closest to the external urethral sphincter has occurred, the element 7 will remain in position and allow urinary passage without obstructing the function of the sphincter.

The wire design of the element 7 is of particular advantage when the element 7 is to be removed or retracted from a body cavity because the element 7 of a shape memory alloy becomes soft when it is cooled. The element 7 may be removed by grasping in any part of the helically wound wire and subsequently pulling the coil out of the cavity as a wire. Furthermore, the element 7 may have a different design than a coiled wire and the element may be made of other alloys so when cooled the element 7 becomes super elastic and is retractable by folding up the element 7 before retraction.

Figure 7:
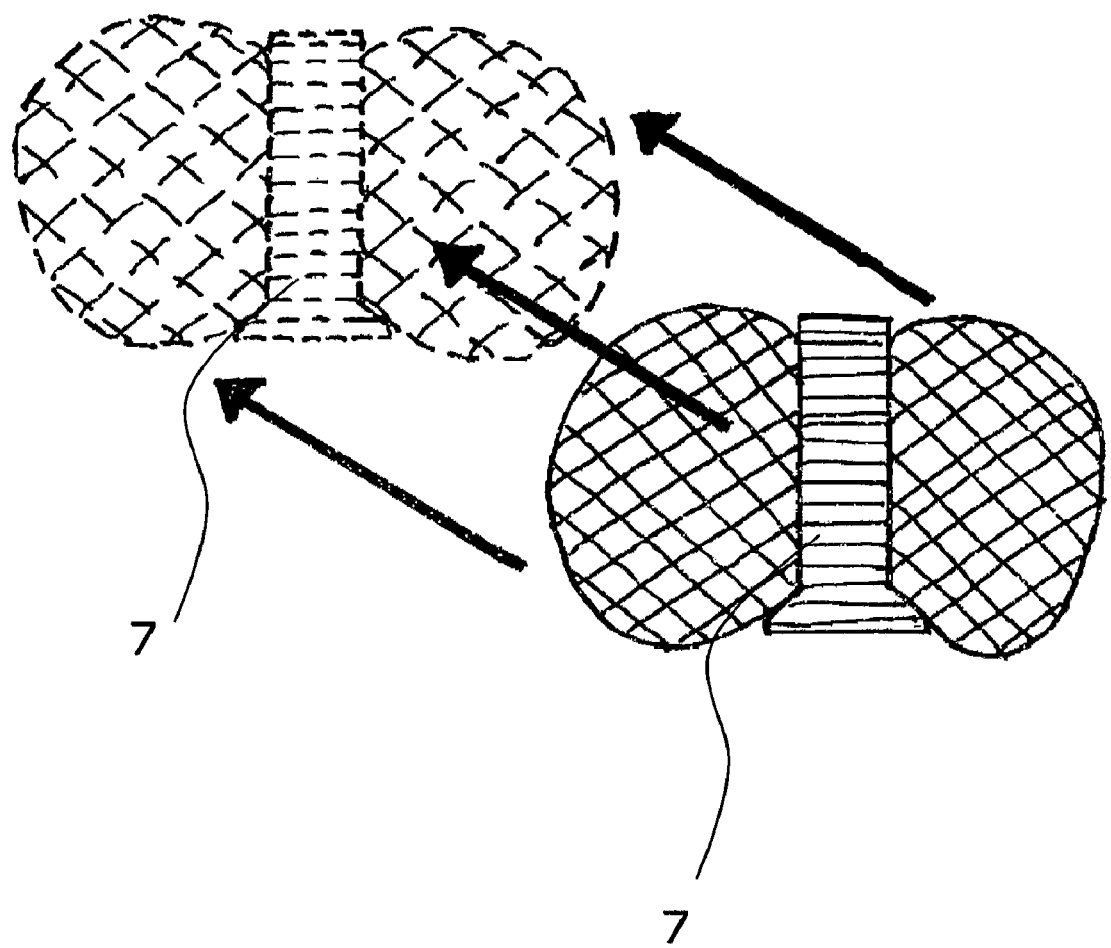
FIG. 7 shows a three-dimensional element having been inserted into the natural cavity a urethra of a male.
Figure 8:
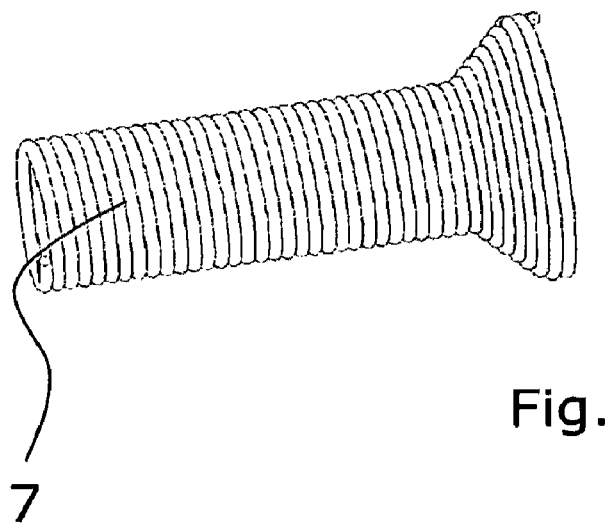
FIG. 8 shows an example of a three-dimensional element.
Figure 9:
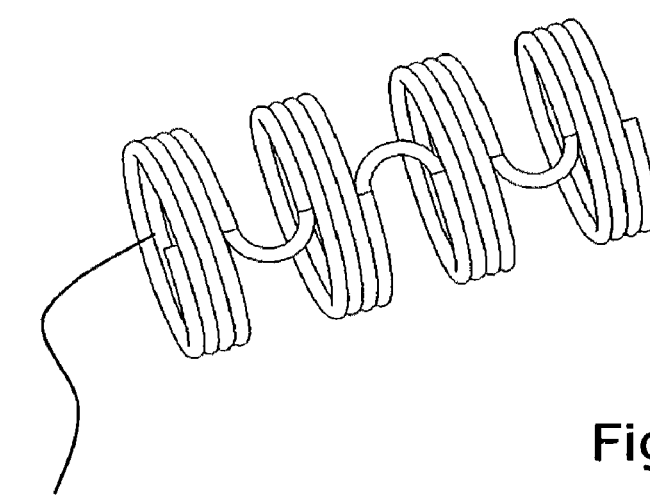
Figure 10:
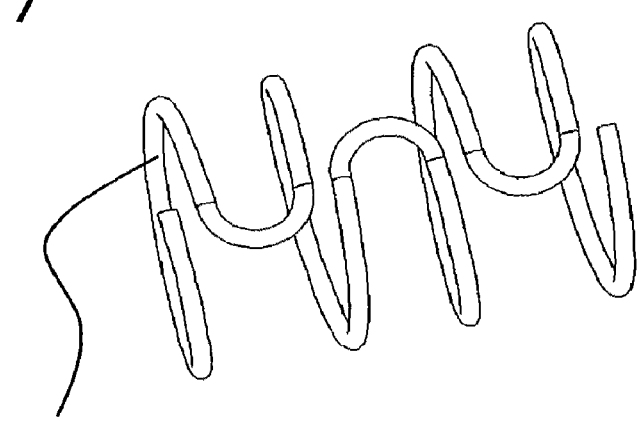
Figure 13:
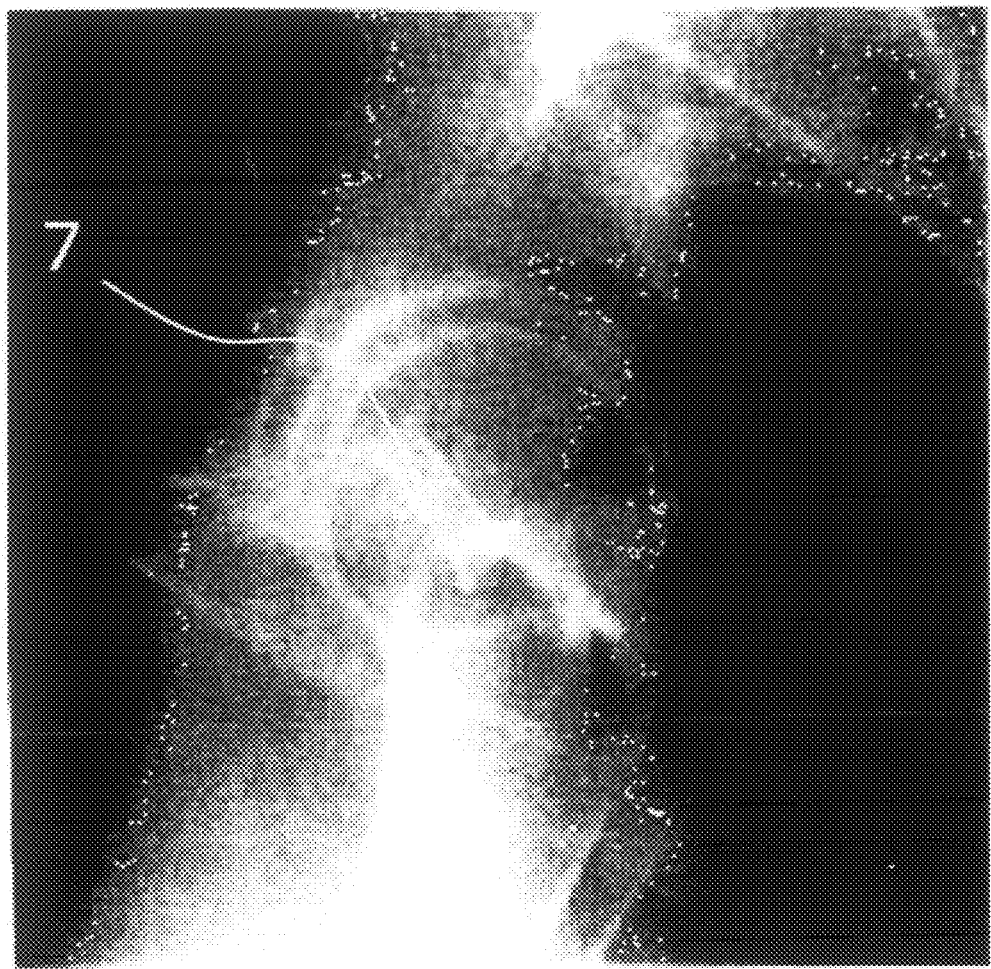

A further advantage of using a three-dimensional element 7 with a kind of locking mechanism is that the element 7 will move together with the tumor 6 during respiration or other partly movements of the human or animal body or during total movement of the same body as shown in FIG. 7. Due to the fact that the element 7 moves with substantially no relative movement in relation to the tumor 6, the irradiation equipment 2 may be adjusted in relation to the possible movement of the three-dimensional element 7 in order to accurately irradiate the tumor 6. In an image 4 produced by the irradiation equipment 2 the computer is not able to detect the tumor 6 since it is not visible in such image 4. However, a three-dimensional element 7 made of metal, such as stainless steel, titanium, platinum, palladium, gold, nickel-titanium and other alloys thereof is easier to detect in such an image 4. Therefore, a possible momentary movement of the element 7 is also detectable and the irradiation equipment 2 may be adjusted to equalize such a momentary movement.

The element 7 may also be of other biologically compatible materials, such as polymers and biological material being detectable in some images.

The three-dimensional element 7 may have all kinds of shapes detectable in image 4 derived and produced by all kinds of medical imaging equipment, said shape resulting in a predefined geometrically structure in said image 4. In order to monitor a possible movement, the predefined geometrically structure is identified in the image 4 and the adjusting of the irradiation equipment 2 may either move the body or properly adjust the position of other parameters of the irradiation equipment 2 in response to this movement.

When using the aforementioned element 7 inserted in the urethra in the vicinity of the prostate the predefined geometrically structure may be the diameter of the helically wound coil or the pitch distance between the windings of the coil. This geometrically structure gives a number of detectable points and is automatically detectable in the image 4 by image processing being implemented on a computer.

Another predefined geometrically structure of the element 7 may be the angle v between the straight part of the element 7 shown in FIG. 7 and the conical part or the predefined geometrically structure may be transition point in which the straight part of the element 7 and the conically part of the coil intersect. This detection, like the aforementioned ways of detection, also provides a three-dimensional positioning of the element 7.

Elements 7 and other kinds of endoluminal prosthesis are often manufactured in various lengths and the aforementioned predefined geometrically structure is independent of this variation in the length of stents and other endoluminal prosthesis.

The three-dimensional element 7 may, as mentioned above, possess all kinds of shapes giving a recognizable defined geometrically structure in the aforementioned image 4. Examples of such other shapes are shown in FIG. 8-11. Instead of a helically wound kind of coil as shown in these figures the three-dimensional element 7 may be a tube having a solid wall and/or an expandable part or different kinds of locking mechanisms. The wall of the tubular element 7 can be made from wire being wound in different patterns, such as cross-patterns, knitting-patterns or the like. The three-dimensional element 7 may, in another aspect of the present invention, be an implant or the reference may be such implant.

By the term mega-voltage equipment is meant all sorts of electron accelerators operating over 150 kV, preferably above 1 MV, and preferably below 50 MV. Such an electron accelerator may be the irradiation equipment 2 used for treating the patient by irradiating the tumor 6.

By medical imaging equipment is meant all kinds of equipment usable for producing the image 4 of disordered tissue and the three-dimensional element 7. Such equipment may be Magnetic Resonance scan (MR-scan), Nuclear Magnetic Resonance scan (NMR-scan), Magnetic Resonance Image scan (MRI-scan), Computerized Tomography scan (CT-scan), Cone Beam CT-scan, Positron Emission Tomography (PET), Single Positron Emission Computed Tomography (SPECT), Single Positron Emission Tomography (SPET), Image-Guided-Radiation-Therapy (IGRT), Ultrasound-scan, or X-ray, high-energy photons equipment or high voltage equipment.

The term shape memory alloy is defined as a metal having transformation from martensite to austenite at a certain temperature range (Austenite Start to Austenite Finish (AS to AF)). Within this temperature range (AS to AF) the expansion of the three-dimensional element 7 starts and the expansion stops when all the martensite is transformed into austenite. The element 7 "remembers" at this temperature range (AS to AF) its original shape. At another temperature range (Martensite Start to Martensite Finish (MS to MF)) the alloy reverses to martensite. Below this other temperature (MF) the element 7 is easily deformable by hand and the element 7 may therefore be easily deformable inside the body cavity and retracted through the natural opening in which the element 7 was inserted. Alternatively the element may be retracted through another natural opening than the one through which it was inserted. The shape memory alloy may also be called temperature-activated alloy.

The term shape memory alloy may also be a metal having super elastic properties at a certain temperature, such as about 37° C., being the body temperature, and a plasticity at a another temperature, such as below 0° C. By the wording super elastic properties is meant an alloy which can be elastically deformed up to very high deformation rates compared to other metals and which alloy does not necessarily have a temperature (AS) at which the material is capable of remembering an original shape.

The shape memory alloy may be a nickel-titanium alloy, a nickel-titanium-cobalt alloy, other transition and precious metal alloys or thermoplastic heat settable material exhibiting shape memory characteristics. Heating of the wire may be accomplished by induction heating, immersion heating, application of RF energy, or by flushing the area of the three-dimensional element 7 with a fluid at the specified temperature.

The invention claimed is:

1. A method for locating a disordered tissue in a human body or animal body, such as a tumor, and for guiding an irradiation equipment located outside the body for treatment of the disordered tissue in the body, comprising the steps of:
    initially performing one of the following steps: inserting into a cavity of the human body or the animal body, or maintaining in position in a cavity of the human body or the animal body, at least one single, integral three-dimensional element, the at least one three-dimensional element having a locking mechanism for locking the three-dimensional element in a position relative to the disordered tissue so as to ensure that the three-dimensional element will have substantially no movement relative to the disordered tissue, and the at least one three-dimensional element having a geometrical structure with a number of points that are detectable in an image of the three-dimensional element,
    identifying, in an image, the at least one single, integral three-dimensional element visible in the image of the human body or the animal body in relation to the disordered tissue,
    establishing, in the image, a preliminary position of the at least one single, integral three-dimensional element, visible in the image, in relation to a reference,
    establishing, in the image, a preliminary position of the irradiation equipment in relation to the reference, in order to establish a preliminary set-up of the irradiation equipment in relation to the reference, and
    adjusting the irradiation equipment in relation to the reference in response to the preliminary position or a subsequent position of the at least one single, integral three-dimensional element in relation to the reference.

2. A method according to claim 1, wherein the step of establishing a preliminary position of the irradiation equipment in relation to the reference is performed in order to establish a preliminary set-up of a mutual relationship between the irradiation equipment and the reference.

3. A method according to claim 1, wherein the step of establishing a preliminary position of the irradiation equipment in relation to the reference is performed in order to establish a preliminary set-up of a number of selected irradiation parameters of the irradiation equipment.

4. A method according to claim 1, wherein the step of adjusting is a step of adjusting the mutual relationship between the irradiation equipment and the reference in response to the possible movement of the three-dimensional element in relation to the reference.

5. A method according to claim 1, wherein the step of adjusting is a step of adjusting at least some of the number of selected irradiation parameters of the irradiation equipment in response to the preliminary position of the radiation equipment.

6. A method according to claim 1, wherein the step of adjusting is a step of adjusting at least some of the number of selected irradiation parameters of the irradiation equipment in response to the possible movement of the three-dimensional element.

7. A method according to claim 1, the method comprising the further step of monitoring a possible movement of the three-dimensional element in relation to the irradiation equipment.

8. A method according to claim 1, wherein the reference is a previous image of the three-dimensional element having been inserted into the cavity of the body.

9. A method according to claim 1, wherein inserting of the three-dimensional element is performed through a natural opening of the body without substantially penetrating any tissue of the body.

10. A method according to claim 1, further comprising the step of retracting the three-dimensional element through a natural opening of the body without substantially penetrating any tissue of the body.

11. A method according to claim 1, wherein the step of monitoring and adjusting is performed during treatment of a disordered tissue such as a tumor.

12. A method according to claim 1, wherein at least a part of the three-dimensional element has a shape allowing passage of a liquid, gas or solid inside the cavity in which the three-dimensional element is positioned.

13. A method according to claim 1, wherein at least a part of the three-dimensional element is expandable towards the cavity from inside the cavity, when released in the cavity.

14. A method according to claim 1, wherein at least a part of the three-dimensional element has a tubular shape allowing passage of a liquid, gas or solid inside the cavity in which the three-dimensional element is positioned.

15. A method according to claim 1, wherein the three-dimensional element is a tubular endoluminal prosthesis.

16. A method according to claim 1, wherein the three-dimensional element is a helical coil of at least one wire.

17. A method according to claim 1, wherein the three-dimensional element is made of a biologically compatible material, such as polymers, biological material or metal, such as stainless steel, titanium, platinum, palladium, nickel-titanium and other alloys or combinations of any of these materials.

18. A method according to claim 1, wherein the three-dimensional element is made of a shape memory alloy having a transition temperature with a one-way-memory effect at a temperature above body temperature, preferably at a temperature between 37° C. and 50° C.

19. A method according to claim 1, wherein the three-dimensional element is made of a material being plastically deformable by hand at a temperature below body temperature, preferably at a temperature below 37° C., more preferred at a temperature below 20° C. and above 5° C.

20. A method according to claim 1, wherein the three-dimensional element is made of a shape memory alloy being super elastic at body temperature, preferably being super elastic at 37° C.

21. A method according to claim 1, wherein the image is a two-dimensional projection image, and wherein the image is derived and processed by medical imaging equipment.

22. A method according to claim 21, wherein the medical imaging equipment is Magnetic Resonance scan (MR-scan), Nuclear Magnetic Resonance scan (NMR-scan), Magnetic Resonance Image scan (MRI-scan), Computerized Tomography scan (CT-scan), Cone Beam CT-scan, Positron Emission Tomography (PET), Single Positron Emission Computed Tomography (SPECT), Single Positron Emission Tomography (SPET), Image-Guided-Radiation-Therapy (IGRT), Ultrasound-scan, or X-ray, high-energy photons equipment or high voltage equipment.

23. A method according to claim 1, wherein the image is a three-dimensional projection image, and wherein the image is derived and processed by medical imaging equipment.

24. A method according to claim 23, wherein the medical imaging equipment is Magnetic Resonance scan (MR-scan), Nuclear Magnetic Resonance scan (NMR-scan), Magnetic Resonance Image scan (MRI-scan), Computerized Tomography scan (CT-scan), Cone Beam CT-scan, Positron Emission Tomography (PET), Single Positron Emission Computed Tomography (SPECT), Single Positron Emission Tomography (SPET), Image-Guided-Radiation-Therapy (IGRT), Ultrasound-scan, or X-ray, high-energy photons equipment or high voltage equipment.

25. A method according to claim 1, wherein the image is derived and processed by utilizing energy of the irradiation equipment.

26. A method according to claim 1, wherein the image is derived and processed by utilizing energy from the treatment irradiation beam.

27. A method according to claim 1, wherein the three-dimensional element has a design enabling insertion and/or retraction of the three-dimensional element with endoscopic equipment.

28. A method according to claim 1, wherein said cavity has at least one surrounding wall, and wherein the three-dimensional element has a collapsible design, enabling a collapsed design when inserting the three-dimensional element in the cavity, and enabling an expanded design when the three-dimensional element has been positioned in the cavity.

29. A method according to claim 1, wherein the reference is located in a position inside the human body or the animal body.

30. A method according to claim 1, wherein the reference is located in a position outside the human body or the animal body.

31. A method according to claim 1, wherein the reference is a structure being part of the human body or the animal body such as a bone structure.

32. A method according to claim 1, wherein the reference is an image-detectable object, not being part of the human body or the animal body.

33. An apparatus for carrying out the method according to claim 1, comprising image deriving equipment for identifying the three-dimensional element, image processing equipment for establishing a preliminary position of the three-dimensional element and the irradiation equipment, image deriving equipment for monitoring a possible movement of the three-dimensional element and equipment guiding activators for adjusting the irradiation equipment or the human body or the animal body in response to the movement.

* * * * *